United States Patent [19]

Antonucci et al.

[11] Patent Number: 5,380,901
[45] Date of Patent: Jan. 10, 1995

[54] MULTIFUNCTIONAL ACRYLATES AND THE SYNTHESIS THEREOF

[75] Inventors: Joseph M. Antonucci, Kensington; Jeffrey W. Stansbury, Gaithersburg, both of Md.; Guo-Wei Cheng, Sichuan, China

[73] Assignee: The United States of America as represented by the Secretary of Commerce, Washington, D.C.

[21] Appl. No.: 828,316

[22] Filed: Jan. 30, 1992

[51] Int. Cl.$^6$ ............................................. C07F 7/08
[52] U.S. Cl. ......................................... 556/440; 560/144; 560/254; 560/261
[58] Field of Search ............... 556/440; 560/144, 254, 560/261

[56] References Cited

U.S. PATENT DOCUMENTS

| | | | |
|---|---|---|---|
| 3,066,165 | 11/1962 | Rosenthal et al. | 260/484 |
| 3,288,883 | 11/1966 | Temin et al. | 260/836 |
| 3,743,669 | 7/1973 | Hillman et al. | 260/465.6 |
| 3,810,938 | 5/1974 | Schmitt et al. | 260/486 R |
| 3,835,090 | 6/1974 | Gander et al. | 260/42.15 |
| 3,923,740 | 12/1975 | Schmitt et al. | 260/47 U A |
| 4,041,061 | 8/1977 | Buck | 260/464 |
| 4,041,062 | 8/1977 | Buck | 260/465 |
| 4,041,063 | 8/1977 | Buck | 260/465.4 |
| 4,067,853 | 1/1978 | Schmitt et al. | 260/47 U A |
| 4,308,014 | 12/1981 | Kawahara et al. | 433/228 |
| 4,330,283 | 5/1982 | Michl et al. | 433/201 |
| 4,406,625 | 9/1983 | Orlowski et al. | 433/228 |
| 4,433,958 | 2/1984 | Fellmen et al. | 433/199 |
| 4,458,087 | 7/1984 | McAlister | 556/465 |

(List continued on next page.)

OTHER PUBLICATIONS

Mathias et al., (Mathias, L. J.; Kusefoglu, S. H.), *Macromolecules*, 1987, 20, pp. 2039–2041.

Mathias et al., (Mathias, L. J.; Kusefoglu, S. H., Ingram, J. E.), *Macromolecules*, 1988, 21, pp. 545–546.

"Synthesis of Novel Polyfluorinated Acrylic Monomers and Oligomers", J. M. Antonucci and J. W. Stansbury, published in Polymer Preprints 34, Mar. 5, 1993.

Stansbury, J. W., *J. Dent Red. 1990, 69, pp. 844–848.*

Mathias, L. J.; Dickerson, C. W., *J. Polym, Sci., Polym, Lett.*, 1990, 28, p. 175.

Butler, G. B., In: Proceedings of the International Symposium on Macromolecules, E. B. Mano, Ed., New York: Elsevier *Scientific Publishing Company*, 1975 pp. 57–76.

"*A Facile Synthesis of Novel Fluorinated Multifunctional Acrylates*", Antonucci, J. M., Stansbury J. W., and Cheng, G. W.; NIST Polymer Division, Gaithersburg, Md. 20899.

Antonucci, J. M.; Stansbury, J. W. Cheng, G. W., *Polym. Prepr.* 1990, 31(1), p. 320.

Antonucci, J. M.; Stansbury, J. W. Cheng, G. W., "*A Facile Synthesis of Novel Fluorinated Multifunctional*

(List continued on next page.)

Primary Examiner—Paul F. Shaver
Attorney, Agent, or Firm—Henderson & Sturm

[57] ABSTRACT

The present invention provides a process for converting a hydrophobic siloxane diacrylate, an aromatic fluorinated diacrylate and a hydrophilic polyethylene glycol diacrylate to their respective multifunctional oligomers. Bis(4-acryloxybutyl)tetramethyldisiloxane, prepared from the corresponding diol, is converted to relatively low viscosity, multifunctional oligomers with the use of DMSO. The hydrophilic monomer, polyethylene glycol 400 diacrylate, formed more viscous, water soluble oligomeric products without the need for a solvent. Characterization of these oligomers by infrared spectroscopy and $^1$H NMR supports the assigned structures. Because of the predominant 1,6-arrangement of double bonds in these oligomers, they have a propensity to undergo cyclopolymerization as well as the usual crosslinking associated with the free radical polymerization of multifunctional monomers and oligomers. These novel oligomeric monomers have potential use in dental composites, sealants, adhesives, dentures, contact lenses, biomedical prostheses, cements, drug delivery systems, coatings and caulks.

7 Claims, No Drawings

U.S. PATENT DOCUMENTS

| | | | |
|---|---|---|---|
| 4,572,920 | 2/1986 | Rawls et al. | 523/115 |
| 4,692,537 | 9/1987 | McAlister | 556/484 |
| 4,760,122 | 7/1988 | Nakos et al. | 526/242 |
| 4,778,915 | 10/1988 | Lina et al. | 560/29 |
| 4,843,136 | 6/1989 | Reiners et al. | 526/279 |
| 4,889,948 | 12/1989 | Mathias | 560/181 |
| 4,940,766 | 7/1990 | Gay et al. | 556/440 X |
| 4,946,977 | 8/1990 | Bernhardt et al. | 556/440 |
| 4,981,903 | 1/1991 | Garbe et al. | 589/547 |
| 5,010,141 | 4/1991 | Mueller | 525/276 |
| 5,039,761 | 8/1991 | Ono et al. | 556/440 X |
| 5,117,027 | 5/1992 | Bernhardt et al. | 556/440 |
| 5,145,374 | 9/1992 | Stansbury | 433/228.1 |

OTHER PUBLICATIONS

*Acrylates*"; 199th mtg. Amer. Chem. Soc.; Boston Mass.; Apr. 24, 1990.

"Synthesis of Novel Highly Fluorinated Multifunctional Vinyl Monomers and Oligomers"; 68th General Session of the International Assoc. for Dental Research; Cincinnati Ohio; Mar. 10, 1990; *Polym. Prepr.*, 1990, 31(1).

Marvel, C. S., "*Intramolecular-IntermolecularPolymerization of Nonconjugated Diolefins*"; J. Of Polymer Science 1960 vol. XLVIII, pp. 101–108.

Stansbury, J. W., "*Synthesis and Evaluation of New Oxaspero Monomer for Double Ring Opening Polymerization*"; J. Dent Res., 1992 (71), pp. 1408–1412.

Colletti, R. I. et al. "*Merchanism Study of the Base Catalyzed Ether Formation Involving α-(Hydroxymethyl)Acrylates*"; Macromolecules, 1991, 24, pp. 2043–2047.

Drewes L. et al., *Synth. Commun.*, 1987, 17(3) pp. 291–298.

Amri et al., "*Hydroxyalkylation de la MethylvinylcentoneetDe L'Acrylonitrile en Presence de Diazo-1,4 Bicyclo [2.2.2] Octane,*" 27 Tetrahedron Letters, 1982, pp. 924–926.

Villieras et al., "An easy synthesis of Ethyl α-Halomethylacrylates Using Formaldehyde in Water", *Synthesis, Wittig-Horner Reaction in Heterogeneous Media:1*, 1982, pp. 924–926.

D. Breslow, "*A Polymer That Fights Cancer*", Chemtech, 1985, pp. 302–307.

J. W. Cheng, et al., Abstract #994 "*Synthesis of Novel Highly Fluorinated Multifunctional Vinyl Monomers and Oligomers*", J. Denkes, 1990, 69, p. 233.

MULTIFUNCTIONAL ACRYLATES AND THE SYNTHESIS THEREOF

TECHNICAL FIELD

This invention relates to acrylate compounds, and more particularly to multifunctional acrylate monomers that undergo ambient free radical polymerization.

BACKGROUND ART

Novel difunctional and multifunctional vinyl monomers with a propensity for intra-intramolecular addition polymerization (cyclopolymerization) have been conveniently synthesized from conventional acrylates or diacrylates and paraformaldehyde under neat conditions using 1,4-diazabicyclo[2,2,2]octane (DABCO) as the catalyst

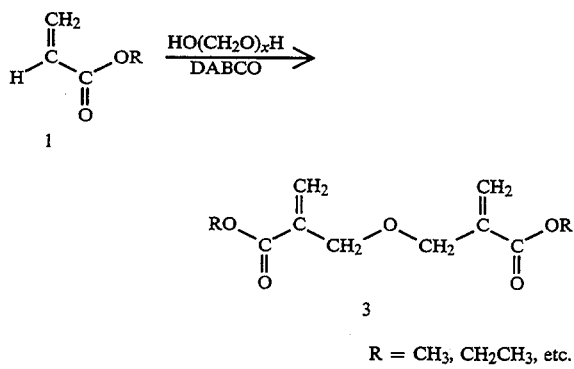

R = $CH_3$, $CH_2CH_3$, etc.

The mechanism for the formation of oxy-bismethacrylates such as 3 from monoacrylates such as 1 (and presumably the oligomeric monomers derived from diacrylates as well) appears to involve an unusual base catalyzed self etherification of the intermediate α-hydroxymethyl acrylate 2

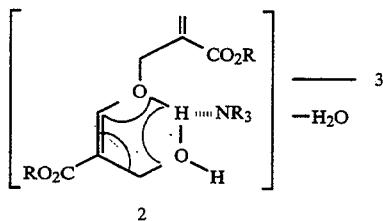

Recently the scope of this interesting reaction was extended to the synthesis of difunctional and oligomeric multifunctional fluorinated monomers from the corresponding mono- and difunctional fluorinated acrylates. In contrast to the solventless conditions used in the transformation of conventional hydrocarbon acrylates, the highly fluorinated starting monomers required the use of a solvent such as dimethyl sulfoxide (DMSO) to achieve their successful conversion to difunctional and oligomeric monomers.

The serendipitous discovery that the DABCO-catalyzed reaction of an acrylate ester and formaldehyde would proceed beyond the initial α-hydroxymethyl acrylate intermediate to a 1,6-diene has uncovered a rich vein of new monomers. The monomers are essentially ether-fused dimethacrylates with the ester groups located externally. This ester functionality can be varied to significantly alter the properties of the monomers and their corresponding polymers. The 1,6-diene configuration in the monomer gives access to an intramolecular cyclization pathway for polymerization. Depending on the polymerization conditions, linear polymer can be formed exclusively via cyclopolymerization or crosslinked polymer can be obtained by a combination of the 1,6-cycloaddition and 1,2-addition polymerization modes.

In addition to the difunctional 1,6-diene monomers, multifunctional oligomers capable of several discrete cyclopolymerizations per chain, thereby yielding highly crosslinked polymers, have been synthesized and evaluated. All these new monomers share several properties that make them attractive prospects for use in dental resins. By virtue of the cyclopolymerization process, high degrees of conversion can be achieved while yielding relatively high modulus polymeric materials. An efficient cyclopolymerization process also offers a route to significantly reduced levels of polymerization shrinkage compared with conventional dimethacrylate polymerizations.

Those aware with these and other developments recognize the need to extend and establish the bounds of this new avenue of chemistry and evaluate novel monomers and their applications.

DISCLOSURE OF THE INVENTION

The present invention provides a process for converting a hydrophobic siloxane diacrylate and a hydrophilic polyethylene glycol diacrylate to their respective multifunctional oligomers. Bis(4-acryloxybutyl)-tetramethyldisiloxane, prepared from the corresponding diol, is converted to relatively low viscosity, multifunctional oligomers with the use of DMSO. The hydrophilic monomer, polyethylene glycol 400 diacrylate, formed more viscous, water soluble oligomeric products without the need for a solvent. Characterization of these oligomers by infrared spectroscopy and $^1H$ NMR supports the assigned structures. Because of the predominant 1,6-arrangement of double bonds in these oligomers, they have a propensity to undergo cyclopolymerization as well as the usual crosslinking associated with the free radical polymerization of multifunctional monomers and oligomers. These novel oligomeric monomers have potential use in dental composites, sealants, adhesives, dentures, biomedical prostheses, cements, contact lenses, drug delivery systems, coatings and caulks.

An object of the present invention is the provision of an improved process for synthesizing multifunctional acrylate monomers having a predominant 1,6-arrangement of double bonds.

A still further object of the present invention is the provision of a process for synthesizing multifunctional acrylates having a propensity to undergo cyclopolymerization.

These and other attributes of the invention will become more clear upon a thorough study of the following description of the best mode for carrying out the invention, particularly when reviewed in conjunction with the examples.

Best Mode for Carrying Out the Invention

The following examples are illustrative of the best mode for carrying out the invention. They are obviously not to be construed as limitative of the invention since various other embodiments can readily be evolved in view of the teachings provided herein.

These examples demonstrate the feasibility of synthesizing multifunctional vinyl oligomers containing ethylene oxide (hydrophilic) or siloxane (hydrophobic) segments.

Synthesis of ethylene oxide based multifunctional vinyl oligomers.

Polyethylene glycol (PEG) 400 diacrylate (average molecular weight=508, Scientific Polymer Products, Inc., Ontario, N.Y.), and paraformaldehyde (95%, Aldrich Chemical Co., Milwaukee, Wis.), 2 mmol (1.016 g) and 4 mmol (0.126 g), respectively, were combined with 0.2 mmol (0.0224 g) DABCO (Aldrich Chemical Co., Milwaukee, Wis.) in a sealed vial which was heated (oil bath) at 90°-95° C. for six hours. The clear, viscous liquid was isolated in ca. 85% yield by column chromatography (silica gel) using methanol as the eluant. As determined by $^1$H NMR spectroscopy (NMR, JEOL GSX-270, Peabody, Mass.), the oligomeric product consisted mainly of segments having the in-chain structures designated by A (1,6-diene) and C (1,4-diene) and end groups such as B as shown below. The ratio of A:B:C was 6:3:1.

In a slightly modified preparation, the same starting mixture of reagents was reacted at 90°-95° C. for 20 hours. The following alternate product isolation procedure was used. The viscous, crude product contained no measurable amount of the PEG 400 diacrylate starting material as determined by $^1$H NMR analysis. The oligomer was washed with several portions of carbon tetrachloride to remove any low molecular weight product as well as the DABCO reaction catalyst. The oligomer was then dissolved in chloroform and dried over anhydrous sodium sulfate. The solvent was removed under reduced pressure (to ca. 5 Pa) to provide the PEG 400 oligomer as a viscous pale yellow oil in ca. 63% yield. Characterization of the product by $^1$H NMR indicated no unreacted acrylate end groups and an average of 3.7 repeat units per oligomer. This corresponds to a molecular weight of ca. 2700 for the oligomer. The repeating diene structure of the oligomer was predominantly 1,6; about 8% of the diene units had the less common 1,4 orientation.

IR (neat) 3465, 2868, 1720, 1636, 1109 cm$^{-1}$. $^1$H NMR (CDCl$_3$) δ 3.65 (internal OC$\underline{H}_2$C$\underline{H}_2$O), 3.77 (OC$\underline{H}_2$CH$_2$O$_2$C), 4.25 (C$\underline{H}_2$OH), 4.28 (C$\underline{H}_2$OCH$_2$), 4.33 (C$\underline{H}_2$O$_2$C), 5.84 (HOCH$_2$C=C$\underline{H}_2$), 5.92 (CH$_2$OCH$_2$C=C$\underline{H}_2$), 6.29 (HOCH$_2$C=C$\underline{H}_2$), 6.34 (CH$_2$OCH$_2$C=C$\underline{H}_2$)

The ethoxylated oligomeric multifunctional vinyl monomer derived from polyethylene glycol (PEG) 200 diacrylate (molecular weight=302, Scientific Polymer Products, Inc., Ontario, N.Y.) was synthesized and characterized in a similar manner. The PEG 200 oligomer, prepared under the same conditions described above (90°-95° C. for 20 hours), contained an average of 4.2 repeat units per oligomer having mainly 1,6-diene units with only 6% 1,4-diene units. The average molecular weight of the PEG 200 oligomer was only ca. 1900 due to the shorter ethylene oxide chain length compared with that in the PEG 400 material; however, it was slightly more viscous than the PEG 400 oligomer.

The following generalized scheme indicates the oligomerization/condensation reaction of formaldehyde with poly(ethylene oxide) based diacrylates.

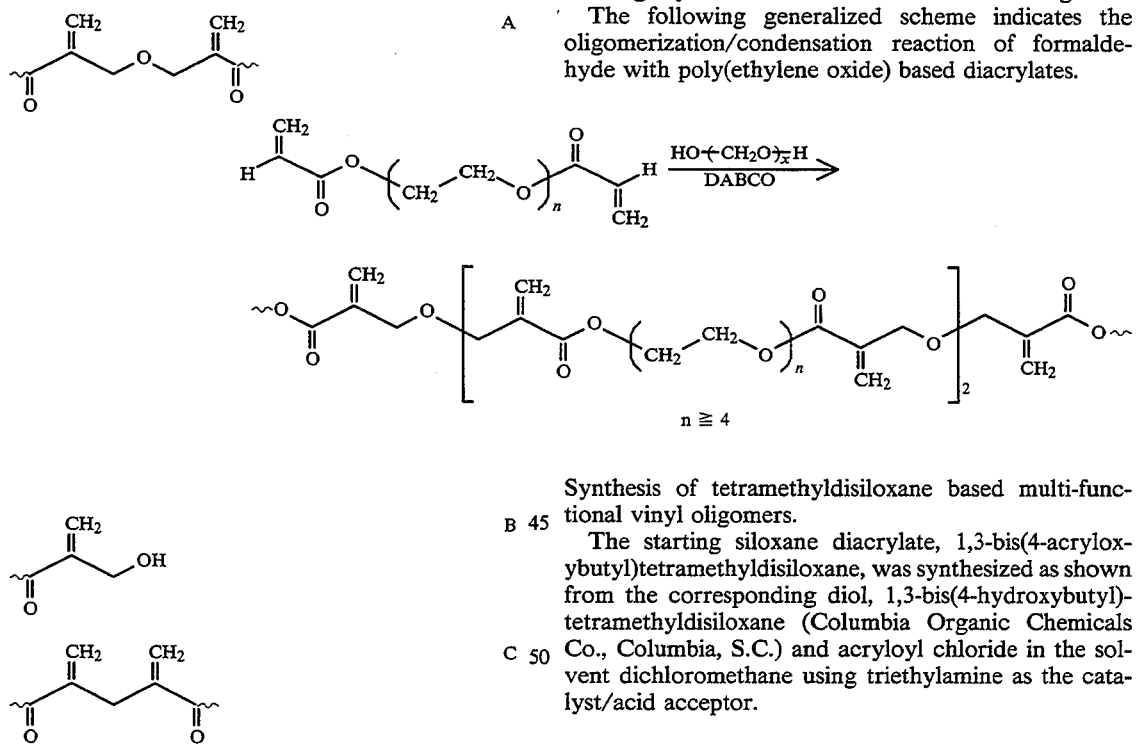

Synthesis of tetramethyldisiloxane based multi-functional vinyl oligomers.

The starting siloxane diacrylate, 1,3-bis(4-acryloxybutyl)tetramethyldisiloxane, was synthesized as shown from the corresponding diol, 1,3-bis(4-hydroxybutyl)-tetramethyldisiloxane (Columbia Organic Chemicals Co., Columbia, S.C.) and acryloyl chloride in the solvent dichloromethane using triethylamine as the catalyst/acid acceptor.

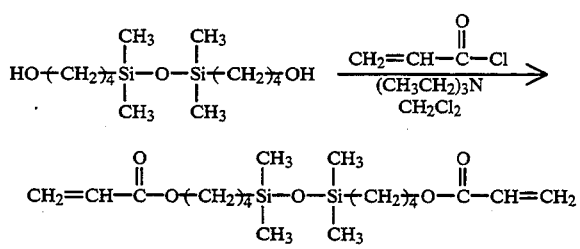

The siloxane diacrylate was isolated in 85% yield and characterized by infrared and $^1$H NMR spectroscopy, respectively.

IR (neat) 2945, 1718, 1631, 1401, 1264, 1254, 1060, 950, 840 cm$^{-1}$ $^1$H NMR (CDCl$_3$) δ 0.00 (s, Si—CH$_3$), 0.51 (t, Si—CH₂), 1.40 (m, Si—CH₂OCH₂), 1.66 (m, O—CH₂—CH₂), 4.12 (t, O—CH₂), 5.78 (d, =CH₂), 6.09 (q, CH₂=CH), 6.38 (d, =CH₂).

The siloxane diacrylate was oligomerized according to the procedure outlined below.

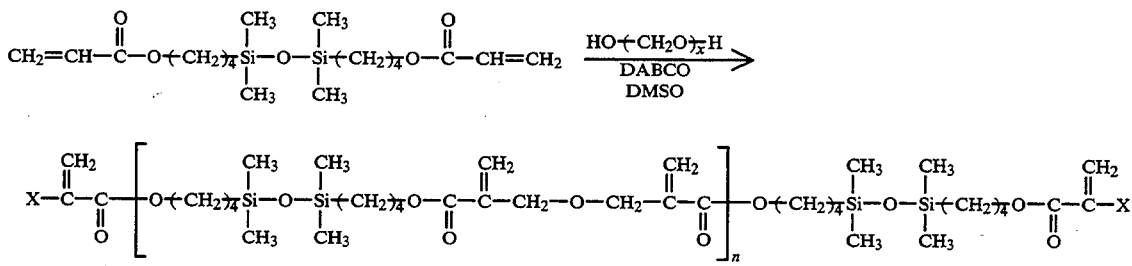

wherein x=—CH₂OH or —H.

A neat mixture of the siloxane diacrylate and DABCO in a molar ration of 1:0.4 was heated for 30 minutes at 80°-85° C. and then transferred to a vial containing 2 equivalents of paraformaldehyde (based on the diacrylate) and DMSO (50% by weight based on the diacrylate). The vial was sealed and heated with stirring (magnetic) at 90° C. (oil bath) for 20 hours. The yellow, viscous liquid was dissolved in ethyl acetate/n-hexane (1:1) and washed with dilute (ca. 5% b.w.) aqueous hydrochloric acid until the extract was at pH 6. The organic phase was dried over anhydrous sodium sulfate, filtered and the solvent was removed by rotary evaporation at room temperature under a moderate vacuum. The pale yellow, slightly viscous residue was then chromatographically separated on silica gel using 20% ethyl acetate in n-hexane to elute the unreacted diacrylate and ethyl acetate to elute the oligomeric product.

IR (neat) 3465, 1718, 1634, 1254, 1164, 1060 cm⁻¹ ¹H NMR (CDCl₃) 0.01 (s, Si—CH₃), 0.48 (t, Si—CH₂), 1.36 (m, Si—CH₂CH₂), 1.64 (m, Si—CH₂CH₂CH₂), 4.12 (t, CH₂O₂C), 4.22 (s, CH₂OCH₂), 4.30 (s, CH₂OH), 5.80 (d, HOCH₂C=CH₂), 5.87 (d, CH₂OCH₂C=CH₂), 6.21 (d, HOCH₂C=CH₂), 6.38 (d, CH₂OCH₂C=CH₂) ¹³C NMR (CDCl₃) 0.2 (Si—CH₃), 17.8 (Si—CH₂), 19.6 (Si—CH₂CH₂), 31.9 (Si—CH₂CH₂CH₂), 62.0 (HOCH₂), 64.4 (CO₂CH₂), 68.7 (CH₂OCH₂), 125.0 and 125.3 (C=CH₂, internal and terminal), 137.0 (CH₂OCH₂C=CH₂), 139.6 (HOCH₂C=CH₂), 165.7 (CH₂OCH₂C9=CH₂)C=O), 166.2 (HOCH₂C(=CH₂)-C=O)

The ¹H NMR also shows a small peak at 5.54 which corresponds to the 1,4-diene linkage, —C(=CH-2)—CH₂—C(=CH₂)—, but this amounts to only about 3% of the structure of the oligomer shown in the above equation. In addition, the ¹³C NMR shows a very small peak at 94.5 which indicates that a trace of 1,8-diene linkage is also present in the oligomer. The ratio of 1,6-diene to terminal hydroxymethyl acrylates is ca. 2:1 which gives a value of n=2 on average for the oligomer. The composition of end groups in the oligomer is x=—CH₂OH (95%) and x=—H (5%).

Results and Discussion

The above examples demonstrate that the unique insertion/condensation reaction of formaldehyde with mono- or difunctional acrylates can be extended to the synthesis of hydrophilic polyethylene oxide and hydrophobic siloxane multifunctional vinyl monomers. The preparation of the hydrophilic oligomers was similar to the procedures used to convert conventional hydrocarbon mono- and diacrylates to the corresponding difunctional and multifunctional vinyl monomers. As expected the hydrophilic oligomers had a predominantly 1,6-diene structure similar to that obtained from oligomers derived from hydrocarbon diacrylates. The siloxane oligomer also had mainly the 1,6 arrangement of double bonds but required the use of the compatibilizing additive or solvent, DMSO, in its synthesis. Previously it was found that DMSO also was necessary to effect the synthesis of analogous highly fluorinated difunctional monomers and oligomers from the corresponding fluoroacrylates.

Because of favorable proximity of many of their double bonds (i.e. the predominance of 1,6-diene units), these oligomers should have a propensity for cyclopolymerization via six membered cyclic rings. Under bulk free radical conditions, which is the common mode of polymerization in dental resin applications, crosslinking also results. The degree of cyclopolymerization versus crosslinking will depend on the 1,4-diene content and other structural features of the oligomer, the type and concentration of comonomers and the conditions of polymerization. Generally, cyclopolymerization will aid in both reducing residual vinyl unsaturation and polymerization shrinkage but will tend to lower the crosslink density of the polymer. The following is an idealized representation of oligomer polymerization or copolymerization showing both cyclization and cross-linking.

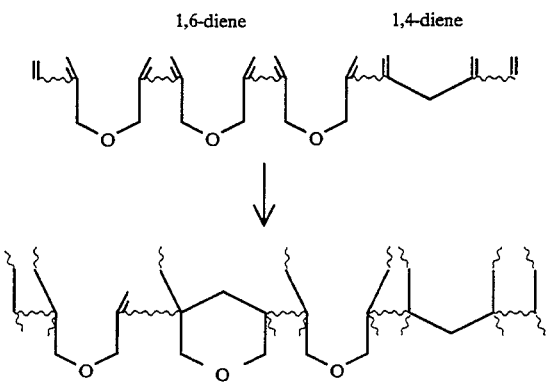

1,6-diene     1,4-diene

The formation of in-chain cyclic structures as shown above is expected to aid in raising the glass transition temperature of these polymers which may somewhat offset the effects of lower degrees of crosslinking.

The hydrophilic and hydrophobic characters of these oligomers should allow the formation of unique homopolymers and copolymers. The poly(ethylene oxide) oligomers are novel hydrogels which should find application in composites, cements and other resin based materials. Their large bulk, cyclopolymerizability and potential for hygroscopic expansion after water uptake all aid in moderating the effects of polymerization contraction. The siloxane oligomers, which combine large bulk, comparatively low viscosity, high flexibility and cyclopolymerizability, offer a facile means of achieving low shrinking, hydrophobic, tough polymer structures suitable for use in a variety of dental, medical and industrial applications.

Synthesis of Multifunctional Fluorinated Oligomeric Monomers.

The combination of hydrocarbon acrylate esters with paraformaldehyde in the presence of DABCO yields the cyclopolymerizable 1,6-diene as the main product. Depending on the ester functionality, the reaction can also produce a 1,4-diene condensation product in concentrations ranging from 0 to approximately 15%. The 1,4-diene configuration in this product would require that a high energy four-membered ring form if cyclopolymerization were to take place through a head-to-tail intramolecular addition, thereby discounting this polymerization pathway. The use of fluorinated acrylate esters derived from $-(CF_2)_n-CH_2OH$ type alcohols in the aldehyde insertion reaction was found to result in predominantly 1,4-diene products due to the electronegativity of the ester group. The synthesis of predominantly fluorinated 1,6-dienes was successful when acrylates derived from fluoro alcohols, $R_fOH$, with $R_f = -CH_2CH_2(CF_2)_n$ were employed; however, these types of fluorinated acrylates or alcohols are extremely scarce. Therefore, in an attempt to prepare 1,6-dienes from readily available fluorinated starting materials, the diacrylate of hexafluorobisphenol A was synthesized and subjected to the standard aldehyde insertion-condensation reaction conditions.

Synthesis of water soluble monomers

Since the ester groups can be varied in the cyclopolymerizable monomers, the functionality can be tailored to fit specific application needs. Preparation of cyclopolymerizable monomers which would be water soluble or water compatible for use as crosslinkable modifying agents for dental and medical adhesives, hybrid glass ionomer cement-composites, polymeric calcium phosphate cements, fluoride and drug release vehicles and contact lenses was undertaken. One approach to this problem involved the use of tetrahydrofurfuryl acrylate in the aldehyde insertion reaction. The major product 11 was obtained in 56% yield.

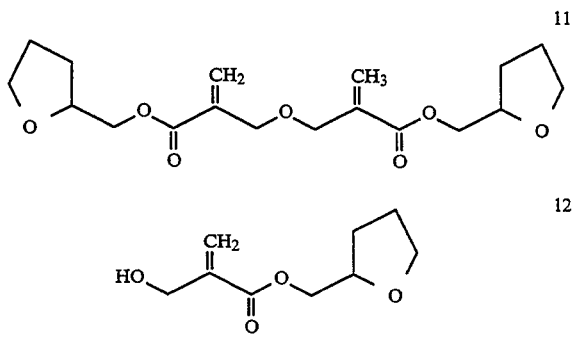

While the difunctional product 11 was significantly more polar in nature than other cyclopolymerizable monomers prepared previously, it was not water soluble. Because of its highly polar nature and facile polymerizability, it is expected to be useful as an adhesion

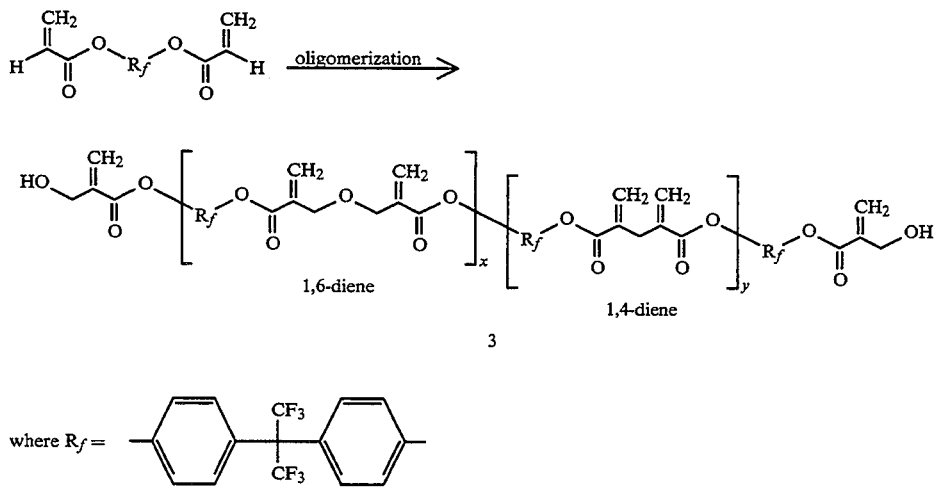

promoting bonding agent. The α-hydroxymethyl intermediate 12 was also isolated from the reaction mixture and this product was quite water soluble and, though not able to cyclopolymerize, is a functional monomer capable of conversion to difunctional and multifunctional monomers and oligomers.

Alternatively, the synthesis of a cyclopolymerizable, difunctional HEMA type derivative was sought. Direct attempts to use 2-hydroxyethyl acrylate (HEA) in the aldehyde insertion reaction were unsuccessful due to complications attributed to the hydroxyl group. Therefore, the alcohol was first protected as the tetrahydropyranyl derivative 13 which was then converted to the 1,6-diene product 14.

Surprisingly, the result was a nonviscous multifunctional oligomer 3 which had internal diene linkages in a 2.1 to 1 ratio favoring the 1,4- over the 1,6-diene. The oligomer had an average of approximately five repeat units per oligomer chain. This type of fluorinated oligomer would be expected to provide a highly crosslinked, hydrophobic matrix; however, it would not be expected to undergo a high degree of cyclopolymerization. However, the combination of low viscosity and relatively high molecular weight in a resin also favors reduced polymerization shrinkage, especially in highly filled composites.

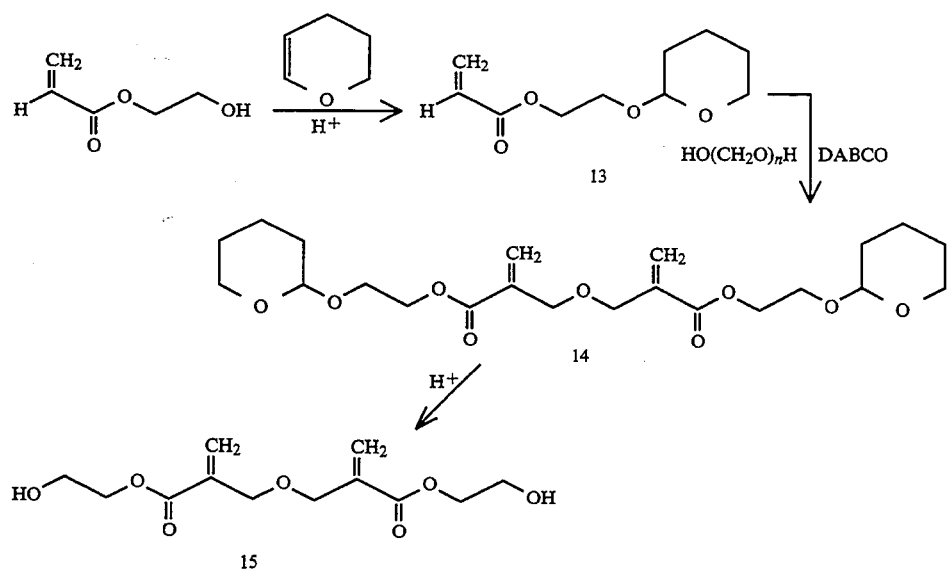

The blocking group was then removed to yield the hydroxyethyl terminated 1,6-diene monomer 15. Like HEA its monofunctional analog, the cyclopolymerizable monomer was completely water soluble. The monomer was polymerized to a crosslinked glassy polymer which swells in water but not in dichloromethane. Aqueous solutions of the monomer can also be polymerized to produce hydrophilic gels which may be of utility in dental and medical applications.

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

We claim:

1. A process for synthesizing multifunctional acrylate monomers and oligomers, comprising the steps of:
   providing a reactant acrylate compound selected from a group consisting of siloxane diacrylate, a polyethylene glycol diacrylate, an aromatic fluorinated diacrylate, and a hydroxylated aliphatic diacrylate; and
   exposing the acrylate compound to reaction conditions comprising a temperature within the range of about 90° C. to about 95° C. for a time within about 6 hours to about 20 hours effective for resulting in multifunctional acrylate monomers and oligomers having predominant 1,6-arrangement of double bonds.

2. The process of claim 1 wherein said acrylate compound is siloxane diacrylate.

3. The process of claim 1 wherein said acrylate compound is aromatic fluorinated diacrylate.

4. The process of claim 1 wherein said acrylate compound is polyethylene glycol diacrylate.

5. The process of claim 1 wherein said acrylate compound is a hydroxylated aliphatic diacrylate.

6. The process of claim 1 wherein DMSO is used as a solvent.

7. The process of claim 3, wherein DMSO is used as a solvent.

* * * * *